United States Patent
Dahmani et al.

(10) Patent No.: US 11,077,255 B2
(45) Date of Patent: Aug. 3, 2021

(54) AUTOMATIC INJECTOR DEVICES AND SYSTEMS FOR CONTROLLED DELIVERY OF DOSAGE AND ASSOCIATED METHODS

(71) Applicant: QuiO Technologies LLC, Chicago, IL (US)

(72) Inventors: Alexander Dahmani, New York, NY (US); Jared Schwartzentruber, New York, NY (US)

(73) Assignee: QuiO Technologies LLC, Chicago, IL (US)

( * ) Notice: Subject to any disclaimer, the term of this patent is extended or adjusted under 35 U.S.C. 154(b) by 378 days.

(21) Appl. No.: 16/084,050

(22) PCT Filed: Mar. 13, 2017

(86) PCT No.: PCT/US2017/022063
§ 371 (c)(1),
(2) Date: Sep. 11, 2018

(87) PCT Pub. No.: WO2017/156523
PCT Pub. Date: Sep. 14, 2017

(65) Prior Publication Data
US 2020/0297933 A1    Sep. 24, 2020

Related U.S. Application Data

(60) Provisional application No. 62/306,855, filed on Mar. 11, 2016.

(51) Int. Cl.
*A61M 5/315* (2006.01)
*A61M 5/142* (2006.01)
*A61M 5/145* (2006.01)
*A61M 5/20* (2006.01)
*A61M 5/24* (2006.01)

(52) U.S. Cl.
CPC ...... *A61M 5/3157* (2013.01); *A61M 5/14248* (2013.01); *A61M 5/14566* (2013.01); *A61M 5/20* (2013.01); *A61M 5/24* (2013.01); *A61M 2005/31588* (2013.01); *A61M 2205/3368* (2013.01); *A61M 2205/3592* (2013.01); *A61M 2205/505* (2013.01); *A61M 2205/52* (2013.01); *A61M 2205/6054* (2013.01); *A61M 2205/8206* (2013.01)

(58) Field of Classification Search
CPC ............... A61M 5/3157; A61M 5/142; A61M 5/14248; A61M 5/14566; A61M 5/20
See application file for complete search history.

(56) References Cited

U.S. PATENT DOCUMENTS

| | | | | |
|---|---|---|---|---|
| 6,656,164 B1 * | 12/2003 | Smith | ..................... | A61M 5/20 604/192 |
| 7,740,612 B2 * | 6/2010 | Hochman | ............... | A61M 5/20 604/121 |
| 8,740,838 B2 * | 6/2014 | Hemond | ............... | A61M 5/486 604/68 |

(Continued)

OTHER PUBLICATIONS

International Search Report and Written Opinion dated May 26, 2017 for International Application No. PCT/2017/022063.

*Primary Examiner* — Laura A Bouchelle
(74) *Attorney, Agent, or Firm* — Perkins Coie LLP

(57) ABSTRACT

Auto-injectors and associated assemblies and methods for delivery of liquid medicament in a controlled manner are disclosed herein.

15 Claims, 13 Drawing Sheets

(56) References Cited

U.S. PATENT DOCUMENTS

| | | |
|---|---|---|
| 2009/0030366 A1 | 1/2009 | Hochman |
| 2011/0184281 A1 | 7/2011 | Fago et al. |
| 2013/0184649 A1 | 7/2013 | Edwards et al. |
| 2018/0353682 A1* | 12/2018 | Laurence .............. A61M 5/315 |
| 2019/0001069 A1* | 1/2019 | Carlsson ........... A61M 5/31568 |

* cited by examiner

AUTOMATIC INJECTOR DEVICES AND SYSTEMS FOR CONTROLLED DELIVERY OF DOSAGE AND ASSOCIATED METHODS

PRIORITY CLAIM

This application is a 371 U.S. National Stage application of International PCT Application No. PCT/US17/22063, filed Mar. 13, 2017, which claims priority to U.S. Provisional Patent Application Ser. No. 62/306,855 which was filed on Mar. 11, 2016, the entire contents of which are incorporated herein by reference and relied upon.

TECHNICAL FIELD

The present technology relates generally to automatic injector devices and associated systems and methods. In particular, several embodiments are directed to automatic injector devices for controlled delivery of a dosage such as a liquid medicament dosage.

BACKGROUND

Auto-injectors are used for parenteral delivery of liquid medicament solutions such as drug solutions, drug suspensions, vaccines, and other medicinal therapies. Many auto-injectors are suitable for the injected delivery of the drug to a patient from pre-filled, disposable cartridges containing the drug. Auto-injectors use an automatic mechanism (e.g., an electrically powered drive unit) to insert a hypodermic needle through the skin of the patient and into the subcutaneous tissue for delivery of the drug. Conveniently, auto-injectors can be used by non-medical users for the subcutaneous administration of drug or by patients for self-administration.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers may be used to identify identical or at least generally similar or analogous components or features.

DETAILED DESCRIPTION

The present technology is directed to apparatuses, systems, and methods for parenteral injection of a liquid medicament into a subject in a controlled manner. In particular, embodiments of the present technology relate to electronic injectors and auto-injector assemblies having disposable dose modules suitable to automatically deliver a pre-determined number of dosages (e.g., a single dose volume) of a liquid medicament. Certain embodiments of the present technology deliver a dose in a controlled manner (within a specified amount of time, at a specified drug temperature, etc.) and/or monitor delivery performance of the electronic injector, for example, to audit the state of the drug and device before, during and/or after drug delivery.

In some arrangements, an electronic injector assembly is configured to deliver a single dose of a liquid medicament in a manner that allows for detection and control of various aspects of the delivery process. For example, a user can detect and control the temperature of the liquid medicament prior to injection. In some embodiments, a user can detect and control a rate of injection of the liquid medicament (e.g., within pre-defined ranges). A rate of injection can be calculated within the context of the use of the injector assemblies described herein. In one embodiment, a rate of injection can be determined based on thermodynamic factors such as medicament viscosity, volume, syringe barrel and needle dimensions, etc. In some embodiments, a user can choose, pre-program and save process program settings that initiate and execute injection of the medicament at different temperatures and/or rates of injection (e.g., for different injection sites, for different medications/drugs, etc.).

Specific details of several embodiments of the technology are described below with reference to FIGS. 1A-9. Although many of the embodiments are described below with respect to devices, systems, and methods for controlled automated injection of medicament into a subject, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-9.

Selected Examples Automated Injectors and Related Devices

Figure 1A:
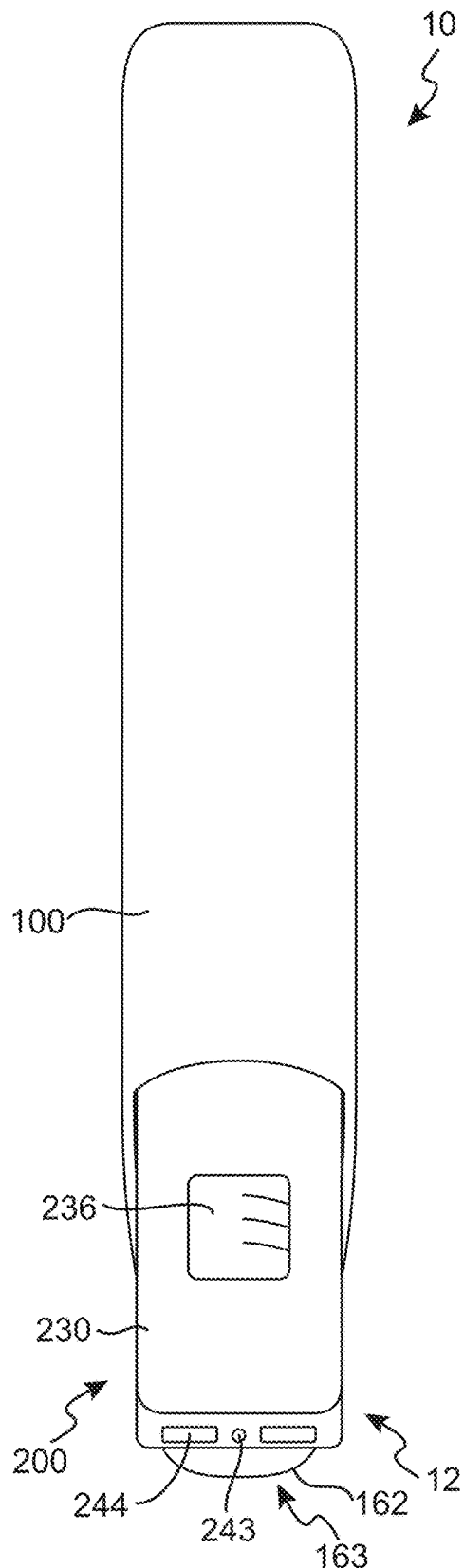
FIGS. 1A and 1B are a front view and a cross-sectional front view, respectively, of an injection assembly that includes an injector and a dose module inserted into the injector in accordance with an embodiment of the present technology.
Figure 1B:
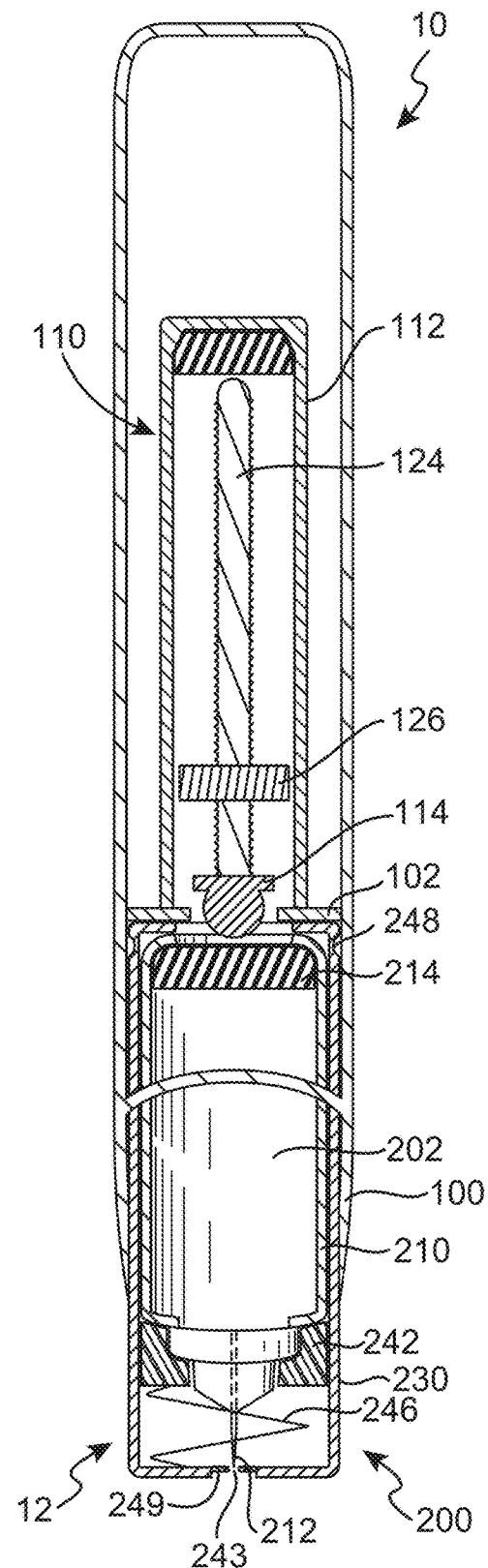
Figure 2:
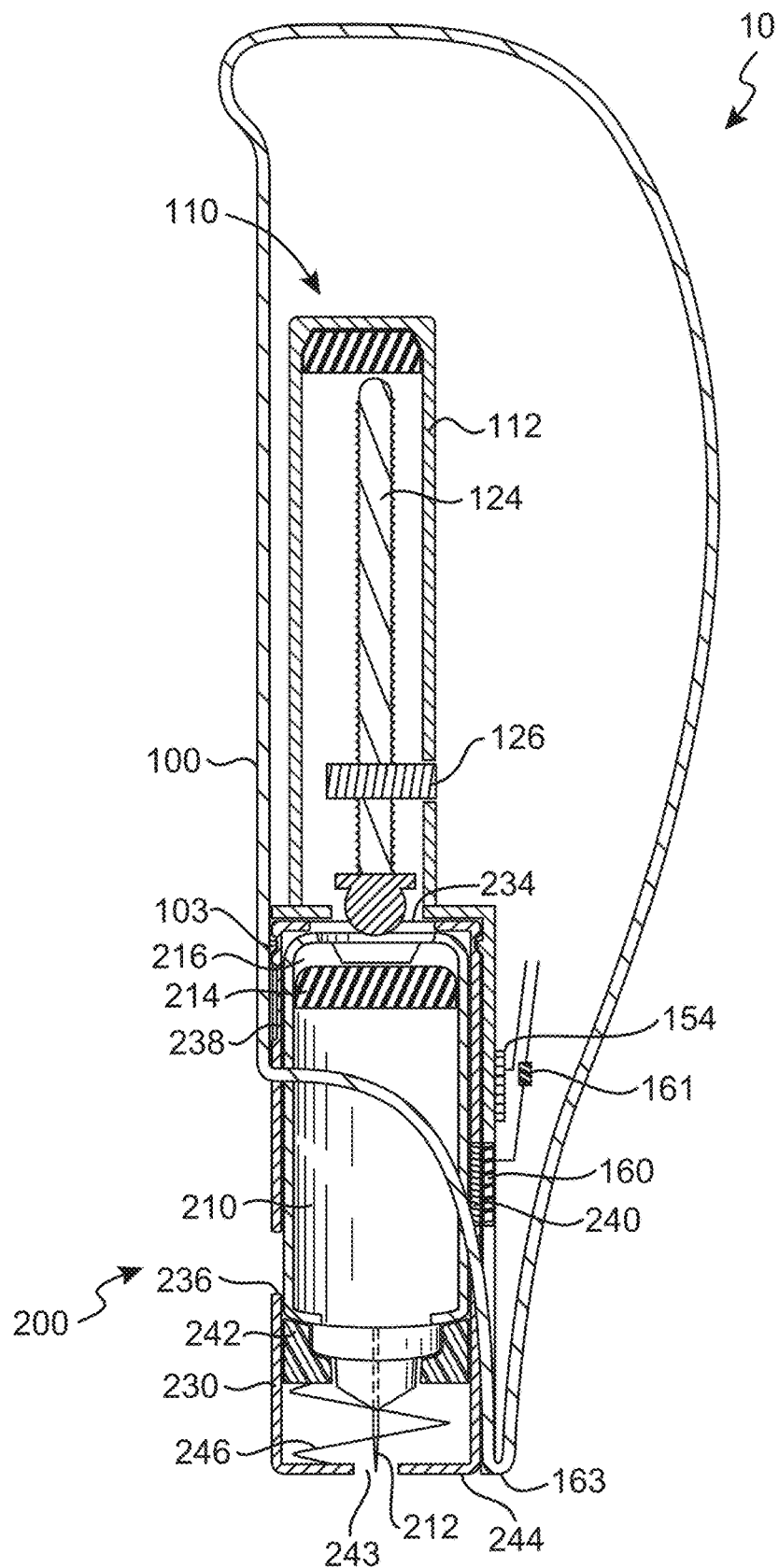
FIG. 2 is a cross-sectional side view of the injector shown in FIGS. 1A and 1B.

FIGS. 1A and 1B are a front view and a cross-sectional front view, respectively, of an injection assembly 10 that can include an injector 100 and a dose module 200 inserted into the injector 100 in accordance with an embodiment of the present technology. FIG. 2 is a cross-sectional side view the injector 100 shown in FIGS. 1A and 1B. Referring to FIGS. 1A-2 together, and in several embodiments, the injector 100 can be a handheld, reusable auto-injector configured to house the dose module 200 (e.g., disposable drug cartridges) in an internal cavity 102 (FIG. 1B) and deliver medicament 202 from a pre-filled hypodermic syringe 210 within the dose module 200 to subcutaneous tissue in a subject via a retractable hypodermal needle 212 (FIGS. 1B and 2).

The internal cavity 102 of the injector 100 is operatively coupled to a drive mechanism 110 housed within the injector 100 and contained within a drive container 112. The drive mechanism 110 is configured to move the needle 220 from a retracted position (shown in FIGS. 1A-2) to an extended position beyond a distal end 12 of the injection assembly 10 (e.g., for penetrating a subject's skin).

Figure 3:
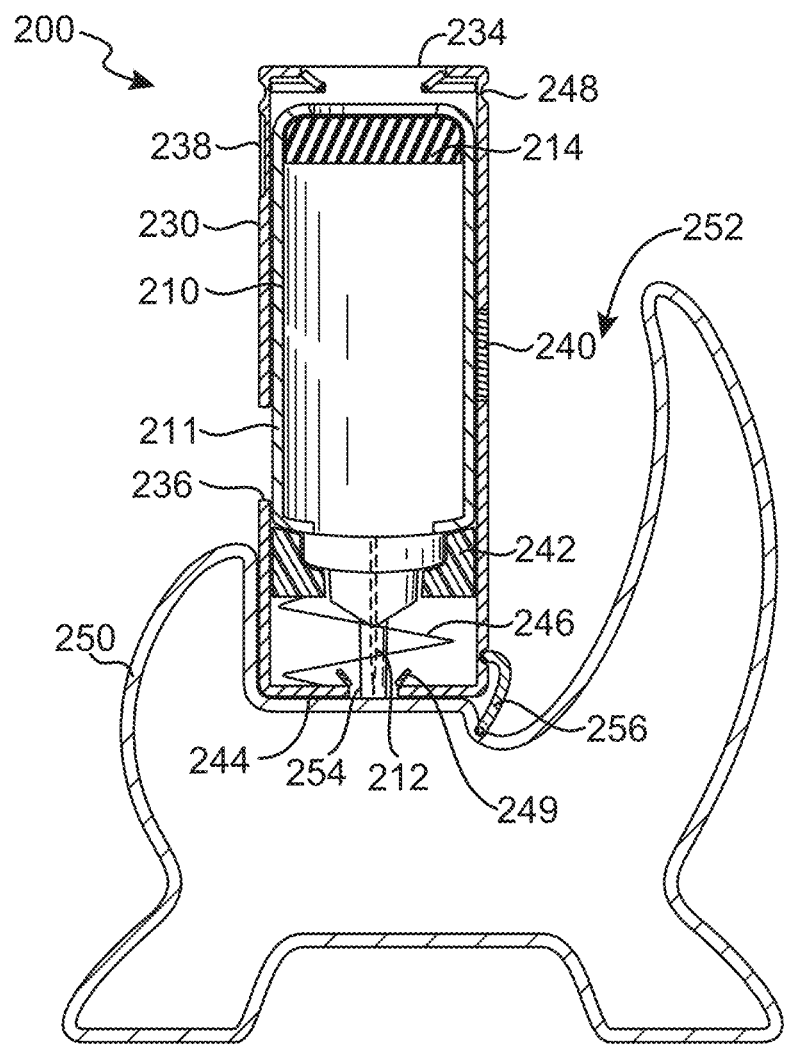
FIG. 3 is a cross-sectional side view of the dose module in accordance with an embodiment of the present technology.
Figure 4:
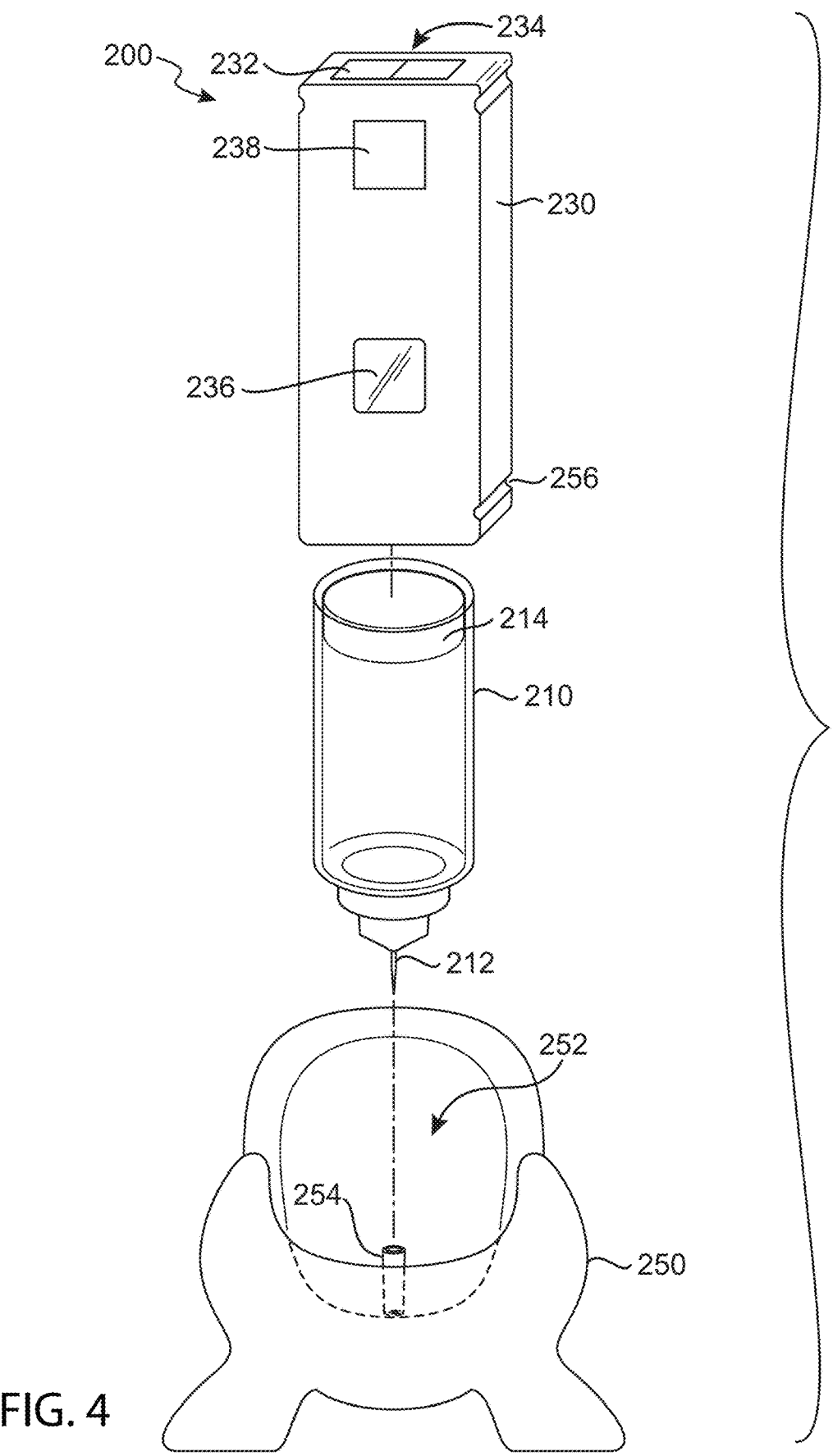
FIG. 4 illustrates a side view of the various components of the dose module shown in FIG. 3 and separated from each other component in accordance with an embodiment of the present technology.

FIG. 3 is a cross-sectional side view of the dose module 200 in accordance with an embodiment of the present technology. FIG. 4 illustrates a side view of the various components of the dose module 200 shown in FIG. 3 and separated from each other component in accordance with an embodiment of the present technology. In the embodiment illustrated in FIGS. 3 and 4, the dose module 200 includes the syringe 210 (e.g., primary container) configured to contain the liquid medicament 202, a cassette 230 (e.g., secondary container) configured to house the syringe 210 and to operably couple with the drive mechanism 110 within the injector 100, and a stand 250 configured to shield the needle 212 inside the cassette 230 and to vertically support the cassette 230 for convenient insertion into the injector 100. Referring to FIGS. 3 and 4 together, the cassette 230 can include a closable access 232 configured to provide a plunger 214 on an upper portion of the syringe 210 access to the drive mechanism 110 when the dosage module is received in the injector 100 (see FIGS. 1B and 2). In some embodiments, the closable access 232 may be one or more moveable doors 234. The cassette 230 can also have a window 236 for viewing the liquid medicament 202 when the cassette 230 is housing the syringe 210 (FIGS. 3 and 4). In one embodiment the window 236 can be clear such that, for example, a person administering the liquid medicament 202 with the injector assembly 10 can view the contents (e.g., volume, etc.) and characteristics (e.g., clarity, precipitation formation, etc.) of the medicament 202 prior to administration. In such embodiments, the syringe 210 can be clear or, in other embodiments, a portion 211 of the syringe 210 aligning with the window 236 is clear such that the viewing person can visualize the syringe contents (FIG. 3).

In some embodiments, the cassette 230 can also include identification information. such as lot number and/or dimensions of the hypodermic syringe 210. lot number of the cassette 230, drug batch and/or expiry date, etc. In one embodiment, the identification information can be stored on an RFID tag 238. In one example, the RFID tag 238 can be a passive tag. In other embodiments, the cassette 230 can include a thermal coupling element or transducer 240 (FIG. 3) in contact with the syringe 210 for transducing the thermal state of the liquid medicament 202 to a thermal sensor 160 located within the inner interior cavity 102 of the injector 100 (shown in FIG. 2).

The dose module 200, as assembled, is illustrated in FIG. 3. As shown, the hypodermic syringe 210 is retained and housed within an interior of the cassette 230. In this embodiment, retention of the syringe 210 is facilitated by a syringe support 242 coupled to the interior of the cassette 230. The syringe support can be a collar or a plurality of shoulder supports configured to retain the syringe 210 at a predetermined distance from a lower surface 244 (e.g., a surface suitable for contact with a subject's skin) of the cassette 230. Attached to the syringe support 242 and resting against the interior lower surface 244 of the cassette 230 is a spring 246 configured to apply resistance against the syringe 210 in a direction away from the lower surface 244 and suitable to assist in retraction of the needle 212 following injection and dose delivery. An upper portion of the cassette 210 can include an indentation 248 configured to be mated with a retention collar 103 within the interior cavity 102 of the injector 100 when the injector assembly is loaded (FIGS. 1A-2).

The stand 250 can be configured to vertically support the cassette 230 and hypodermic syringe 210 within a cradle or cavity 252 in a manner that facilitates transfer to the internal cavity 102 of the injector 100 (FIGS. 3 and 4). The stand 250 can also include a needle sheath 254 to surround and protect the tip of the needle 212 affixed to the hypodermic syringe 210. When cradled in the stand 250, the needle sheath 254 extends past lower cassette doors 249 at the lower surface 244 and into a lower portion of the cassette 230 housing the syringe 210 and needle 212. The stand 250 can further include a cassette latch 256 configured to releasably retain the cassette 230 onto the stand 250 in the vertical orientation. When assembled, the dose module 200 is configured to be received into the internal cavity 102 of the injector 100.

Figure 5:
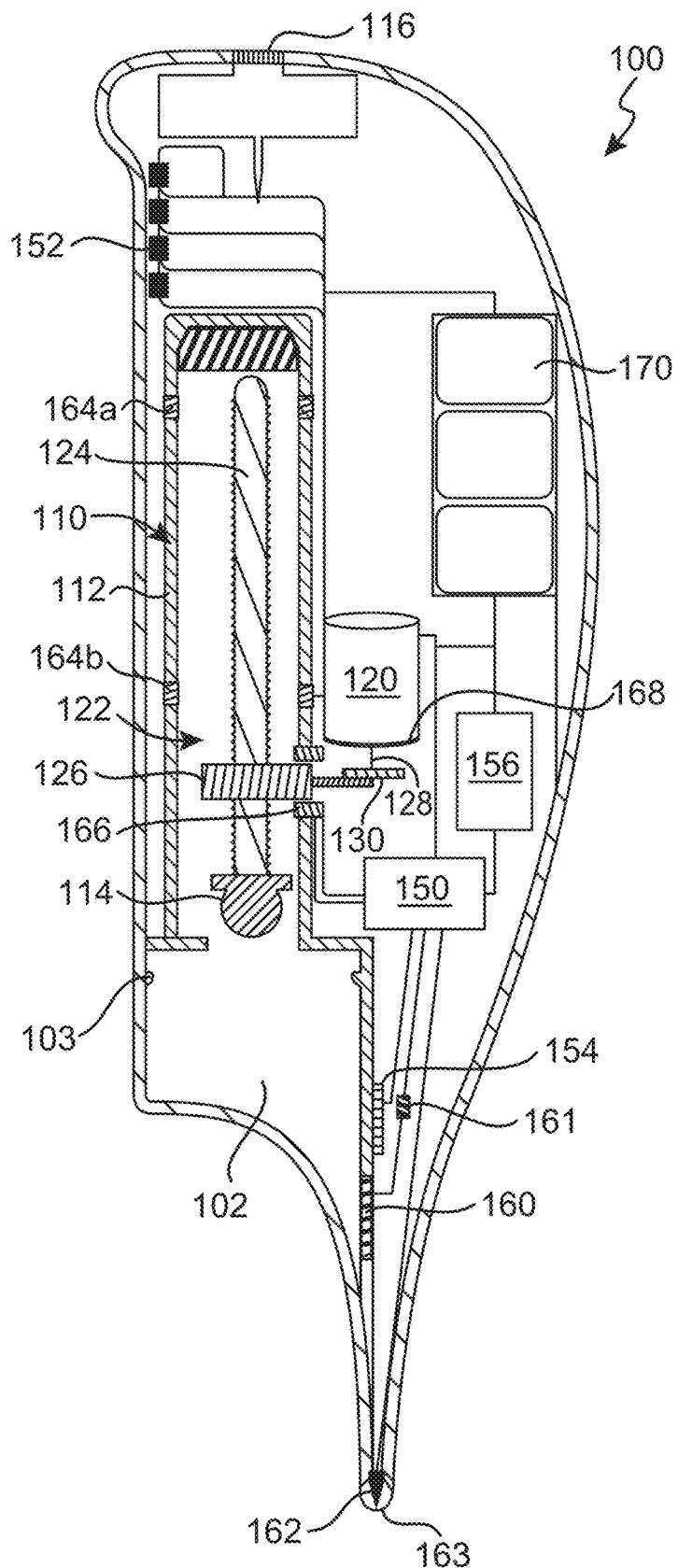
FIG. 5 is a cross-sectional, side view of the injector without the dose module in accordance with an embodiment of the present technology.

FIG. 5 is cross-sectional, side view of the injector 100 without the dose module 200 in accordance with an embodiment of the present technology. In referring to FIGS. 1B, 2 and 5 together, the drive mechanism 110 can be operatively coupled to and/or driven by one or more motors for (a) moving the hypodermal needle 212 from a retracted position to an extended position beyond the lower surface 244 of the cassette 230 (e.g., through a needle aperture 243), and (b) providing force to the plunger 214 in order to expel the liquid medicament 202 from the hypodermic syringe 210 through the needle 212 in a controlled manner. In one arrangement, a motor 120, such as an electronic motor with motion control (e.g., a servo motor), can facilitate both the movement of the hypodermal needle 212 as well as force against the plunger 214. In another embodiment (not shown), a first motor can be configured for a first actuation event of moving the syringe 210 forward within the cassette 230 for the purpose of penetrating the needle 212 into the subject's skin. In such an embodiment, a second motor 120b (e.g., a servo motor) can be configured for a second actuation event of driving the plunger 214 through the syringe 210 at a controlled rate for expelling the liquid medicament 202 into the subject. In various embodiments, the motor(s) 120 may be connected to an actuator 122 comprising a lead screw 124 (e.g., drive piston) and lead nut 126. The actuator 122 can translate the rotational motion of an output shaft 128 into linear motion of the lead nut 126. In some embodiments, a set of gears 130 may be positioned between the output shaft 128 and the actuator 122 for reducing the speed of the motor 120b and/or increasing the torque output. In various embodiments, the gear set 130 can be optimized for delivery of liquid medicaments 202 having varying viscosity.

Referring to FIG. 5, the injector 100 also includes a control system 150, such as a processor (e.g., microprocessor), having instructions for controlling the rate of an injection. In operation, the control system 150 can be based on feedback from one or more sensors (described further below), or from input received from a user via a user interface 152 (e.g., touch screen, buttons). For example, the injector 100 can include an RFID reader 154 for wirelessly reading the identification information on the RFID tag 238 on the cassette 230 (FIG. 4A). In one embodiment, the user interface 152 can be simple with higher-function control available remotely through a mobile and/or web application. The injector 100 can have a radio transceiver 156, such as a Bluetooth Low Energy chip, for sending and receiving information, such as receiving injection instructions from the subject, or sending injection data to a remote database. In some embodiments, the injector 100 can communicate wirelessly with a corresponding application running on a subject's mobile device or computer.

In some arrangements, the injector 100 can have a thermal sensor 160 on the wall of the interior cavity 102 oriented such that the thermal sensor will be in contact with the thermal coupling element 240 (FIG. 3) on the cassette 230 when the cassette is inserted properly into the internal cavity 102. In one embodiment, the thermal sensor 160 can transmit data related to the temperature of the liquid medicament 202 to the control system 150 via a thermoresistor circuit 161. In such arrangements, the control system 150 can alert the user (e.g., subject, patient) when the liquid medicament 202 is at an optimal temperature for injection. A skin sensor 162 (e.g., pressure sensor, contact/touch sensor, temperature sensor, position sensor, etc.) can be positioned on a distal tip 163 of the injector 100 (e.g., a surface aligned with the lower surface 244 of the cassette 230). The skin sensor 162 can indirectly detect contact between the lower surface 244 of the cassette 230 and the subject's skin. In some embodiments, the control system 150 includes memory for storing data related to doses received, injections performed, user-generated injection parameter, etc. For example, the memory can store programs specific for a medicament's rheology. The control system 150 can use input from sensors, such as the thermal sensor 160, in combination with the stored rheology programs in order to calculate a medicament's viscosity. The memory also stores programs for operating the injector 100, such as injection force calculation and corresponding motor speed. The control system's processor can be a master control unit for calculating and performing parameters of a desired injection. The injector 100 can include a power source 170 such as a rechargeable battery for powering the control system 150. The power source 170 may be charged, for example, through a micro-USB port.

Movement of the lead screw 124 can be determined through information received from first and second piston sensors 164a, 164b. The speed of the lead nut 126 can be detected via data received via a rotational sensor 166 and a rotary encoder 168 can measure the speed of the motor 120. When injection instructions are calculated and/or determined, the drive mechanism can engage the plunger 214 of the dose module 200 via contact of a piston head 114 through the closable access 232 of the cassette 210. In some arrangements, a plunger adapter 216 can be positioned between the piston head 114 and the plunger 214 (FIG. 2).

Injection of liquid medicament 202 can be initiated by engagement of an injection button 116 on the injector 100.

Selected Embodiments of Methods Associated with Injection Assemblies

Several suitable methods are disclosed herein and discussed further below: however, one of ordinary skill in the art will recognize a plurality of methods suitable to operate injection assemblies and to deliver a dose of liquid medicament in a controlled manner. With respect to the embodiment illustrated in FIGS. 1A-5, the injector can be used in combination with the dose module for automated delivery of a liquid medicament to a subject. Further methods include steps for delivering a dose of liquid medicament in a controlled manner within a specified time and/or a specified delivery rate. Additional methods include steps for monitoring delivery performance of an injector assembly (e.g., the injector assembly 10 shown in FIGS. 1A-2).

Figure 6:
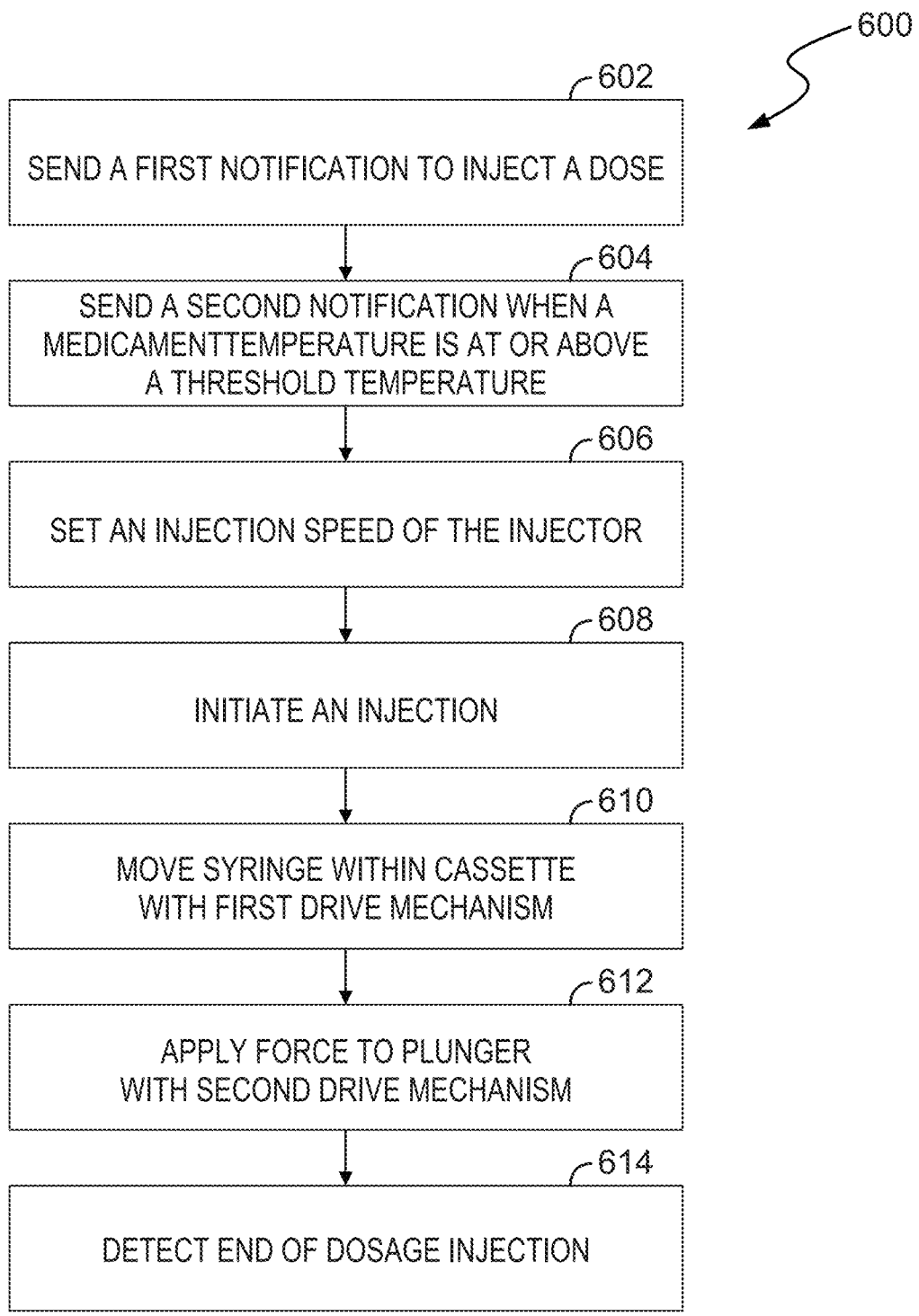
FIG. 6 is a flow diagram illustrating a method for automated delivery of a liquid medicament in accordance with an embodiment of the present technology.

FIG. 6 is a flow diagram illustrating a method 600 for automated delivery of a liquid medicament in accordance with an embodiment of the present technology. The method 600 can begin with sending a first notification reminder (e.g., set by a patient, a healthcare provider, etc.) to a user (e.g., patient) to remind the user to inject a dose of liquid medicament at a predetermined time (block 602). The reminder may be sent by the application, either natively through a software application or by text message to the user's phone. Upon notification, a user can remove a dose module containing a dose of the liquid medicament out of refrigerated storage (if necessary) in order to raise a temperature of the medicament to room temperature, for example. An injector may be loaded with a dosage module cassette containing the syringe by placing the injector over the vertically aligned cassette and moving the injector in a downward motion. The method 600 can continue with sending a second notification reminder to the user when the temperature of the medicament reaches a threshold temperature (e.g., reaches desired injection temperature) (block 604). The method 600 continues with setting an injection speed of the injector (block 606). In some embodiments, and prior to injection of the dosage, the user may select a desired injection speed via the user interface on the injector or wirelessly through a software application. In another embodiment, the injection speed can be a speed selected based on the characteristics of the medicament and/or a manufactures's preference.

The user can remove the injection assembly from the stand (e.g., the dose module stand). In various arrangements, removal of the cassette/syringe portion of the dose module from the stand results in removal of the needle sheath, unsheathing the needle tip within the cassette housing. The lower surface of the cassette and skin sensor on the distal tip of the injector can be positioned at an injection site with the device held at an approximate 90° angle relative to the injection surface. In other embodiments, the lower surface of the cassette can be positioned at other angles relative to the injection surface (e.g., between about 80°-90°, between about 70°-90°, between about 60°-90°, etc.). The method 600 also includes initiating an injection of the medicament when an injection button is engaged (block 608). The button may be activated by compression, or in another embodiment, can be touch sensitive. In certain embodiments, the button may require a prolonged depression (e.g., 2 seconds or longer) in order to prevent misfiring of the injector. In other embodiments, the skin sensor can relay a signal to the processor in conjunction with the activation of the inject button in order for the injection to occur.

Once an injection is initiated, the method 600 includes pushing the syringe forward within the cassette with a first drive mechanism, resulting in the protrusion of the needle beyond the lower surface of the cassette and through a needle aperture into the subject's skin (block 610). The method 600 further includes applying force to the plunger using a second drive mechanism to expel the liquid medicament through the needle at a controlled rate (block 612). In various arrangements, the motor speed can be actively controlled by the control system through, for example, a closed loop feedback mechanism in order to maintain a smooth flow rate at the specified injection speed. The method 600 can also include sensing an end of a dosage injection (block 614). For example, a photodiode/photoreceptor located at a distal end of the drive piston chamber can be disrupted when a drive piston reaches a pre-determined terminal distance, thereby signaling an end of an injection. In such embodiments, the injector may signal to the subject that the injection is complete. In various arrangements, a reverse motor rotation can be used to retract the needle out of the patient and back into the protective housing of the cartridge. In some embodiments, a user does not see the needle during the injection process. The cassette and used syringe can be released and/or removed from the injector for disposal. In various embodiments, data related to the injection (average motor speed, injection speed, sensory data such as kinetic temperature profile, dose module identification information, injection performance, etc.) can be manually or automatically uploaded wirelessly through the application into a secure database.

Figure 7:
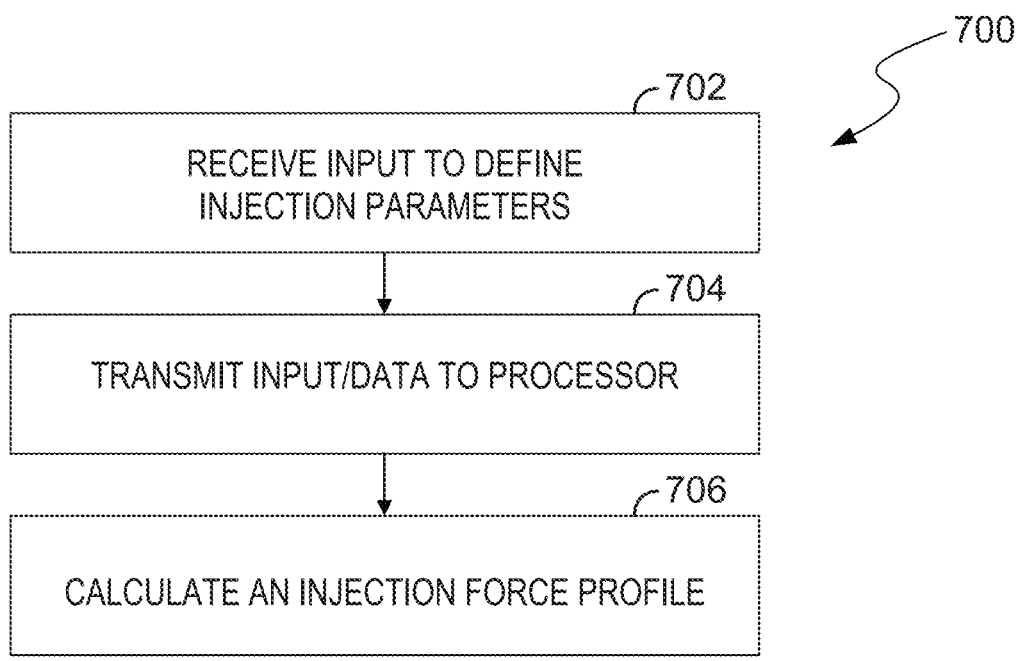
FIG. 7 is a flow diagram illustrating a method for delivering a dose of a biologic solution in a controlled manner in accordance with an embodiment of the present technology.

FIG. 7 is a flow diagram illustrating a method for delivering a dose of a biologic solution in a controlled manner in accordance with an embodiment of the present technology. The method 700 can begin with receiving input from a user, feedback from one or more sensors and/or calculations made by programs stored on the processor memory for defining parameters for an injection of medicament at a specific and/or controlled flow rate (block 702). For example, calculation of an appropriate injection force profile can include receiving information regarding injection speed. Injection speed may be selected by a user (e.g., patient), or alternatively, a standard speed setting may be selected. For injection at a specific flow rate, an appropriate injection force can be calculated. Injection force can depend on multiple parameters, including length of the needle, gauge of the needle, diameter of the syringe barrel, shear rate, and viscosity of the liquid medicament. Viscosity can be unique to each medicament (e.g., drug solution) and dependent on such characteristics as concentration, shear rate and temperature. In some embodiments, drug-specific rheology programs can be stored within the processor's internal memory and can be used in combination with the concentration of the dose, temperature of the syringe, and selected flow rate in order to calculate viscosity. Data for calculating injection force stored on the cassette's identification element and translated by the RFID radar may include, for example, length of the needle, needle gauge, diameter of the syringe barrel and concentration of the dose. The method 700 can also include transmitting all of the inputs/data and sensory information received to the processor (block 704), and calculating an injection force profile (block 706). In various embodiments, the calculations can be performed and the programs can be executed in a specific order at the time the user activates the inject button.

Figure 8:
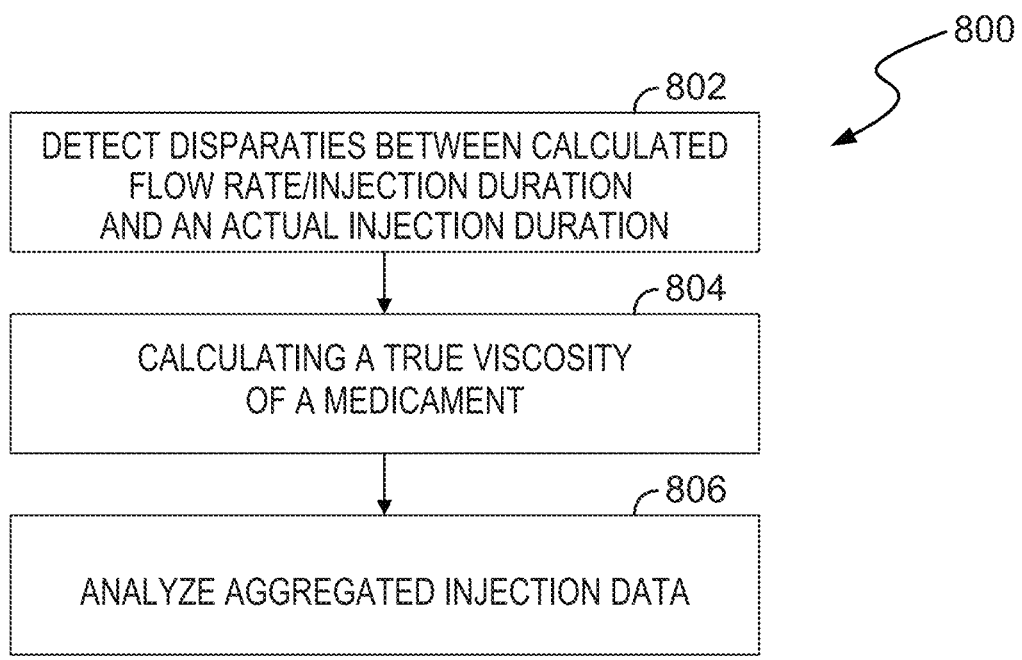
FIG. 8 is a flow diagram illustrating a method for monitoring delivery of a dose of a liquid medicament in accordance with another embodiment of the present technology.

FIG. 8 is a flow diagram illustrating a method 800 for monitoring delivery of a dose of a liquid medicament in accordance with another embodiment of the present technology. The method 800 begins with detecting disparities between a calculated flow rate and injection duration with an actual injection duration, given a constant drug delivery force (block 802). In some embodiments, the control system's processor may use feedback from sensors and a program stored in the memory in order to detect disparities between calculated flow rate and injection duration with actual injection duration. The method 800 can also include calculating a true viscosity of the liquid medicament (block 804). In one example, the actual injection duration may be used in combination with motor performance to calculate a true viscosity of the medicament. Such a disparity between calculated injection duration, based on calculated drug viscosity, and actual injection duration and drug viscosity, may be stored on the device and/or communicated wirelessly through the corresponding application to a remote database. The diagnostic accuracy and sensitivity of the injection audit can further be improved using aggregated data. Accordingly, the method 800 further includes analyzing aggregated injection data (block 806), including the injection audits, which may be wirelessly communicated to a remote database.

Figure 14:
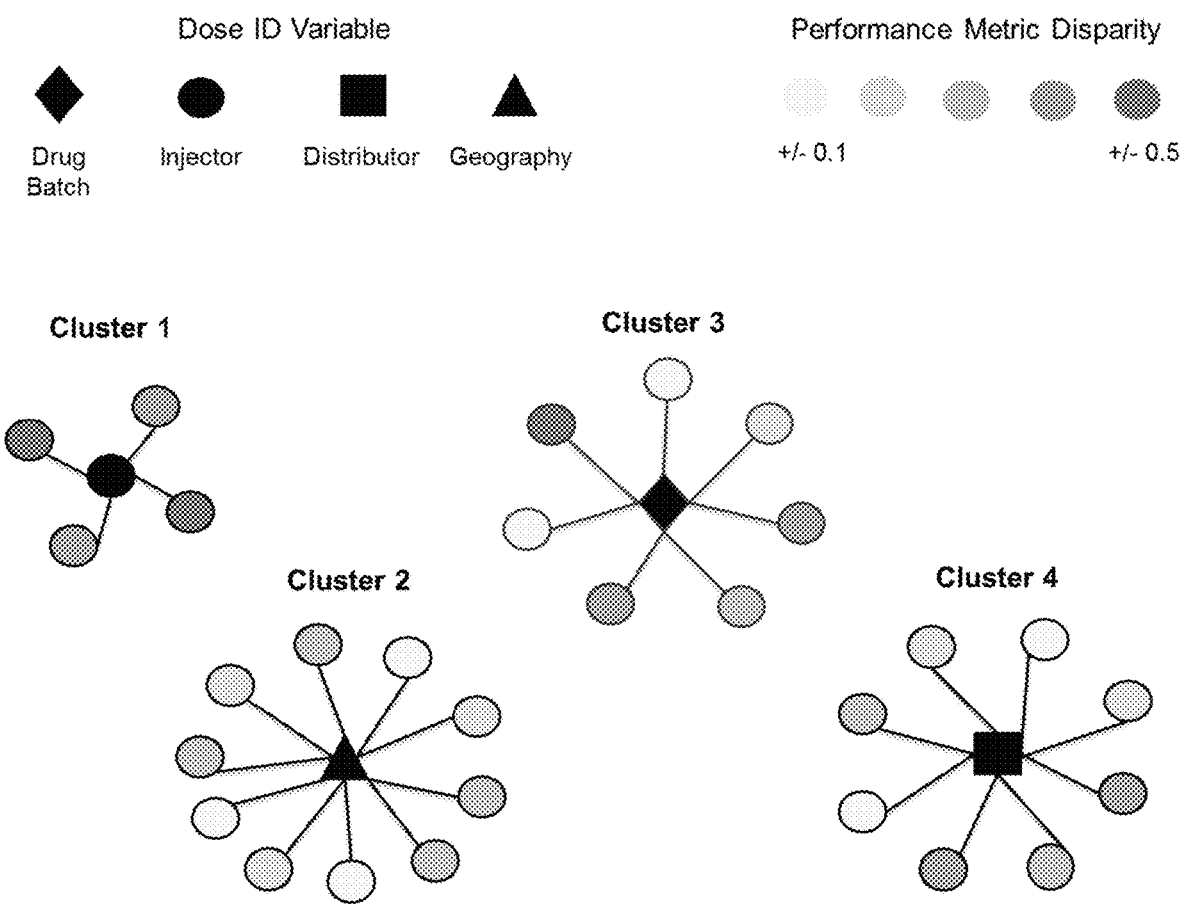
FIG. 14 depicts a representative analysis of aggregate injection audits from multiple doses performed by multiple injectors in the hands of different users.

FIG. 14. depicts a representative analysis of aggregate injection audits from multiple doses performed by multiple injectors in the hands of different users, which can signal the source of a quality issue (e.g., disparity between expected drug delivery performance and recorded drug delivery performance). Drug delivery performance refers to either drug delivery force (given a constant delivery speed), or drug delivery speed (given a constant delivery force). For example, cluster 1 shows multiple injection audits with performance metric disparities from a single injector over multiple doses with no common variable between the dose, which indicates an injector malfunction. Alternatively, injection audits with performance metric disparities reported from multiple injectors with doses that share a common variable stored in the dose ID can reveal the potential source of the quality issue. For example, cluster 2 shows multiple injection audits from different injectors that share a common geographic region where they were administered, suggesting a quality issue such as counterfeiting may have occurred in that location. Cluster 3 shows multiple injection audits with performance metric disparities that derive from the same drug batch, suggesting a production error for that batch of liquid medicament. Cluster 4 shows a single distributor with which multiple injection audits were correlated with, suggesting another quality issue such as improper storage or handling during distribution. Thus, one benefit of the injection audit is quality control over multiple aspects of a treatment (e.g., drug, syringe, injector, distributor, etc.) at the point of care.

Additional Embodiments

Features of the injection assembly components described above and illustrated in FIGS. 1A-5 can be modified to form additional embodiments configured in accordance with the present technology. The memory and storage devices (e.g., remote databases, remote servers, etc.) are computer-readable media that may store instructions that implement at least portions of the described technology. In various arrangements, the data structures (e.g., memory associated with the injector's internal processor. remote server(s), remote database, etc.) and message structures may be stored or transmitted via a data transmission medium, such as a signal on a communications link. Various communications links may be used, such as the Internet, local area network, a wide area network, etc.

Figure 9:
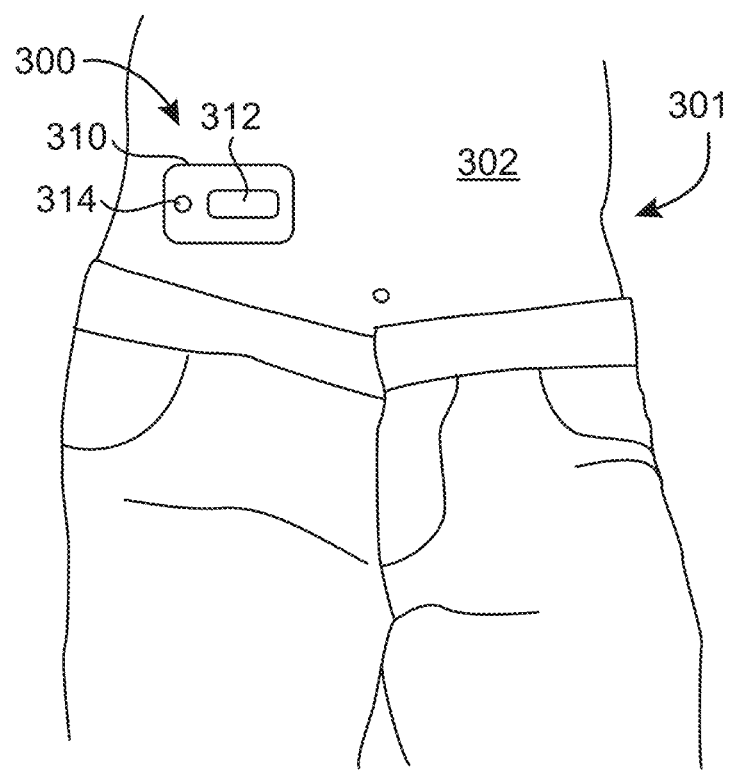
FIG. 9 is a front view of a bolus injector for automated delivery of a liquid medicament to a patient in accordance with an embodiment of the present technology.
Figure 10:
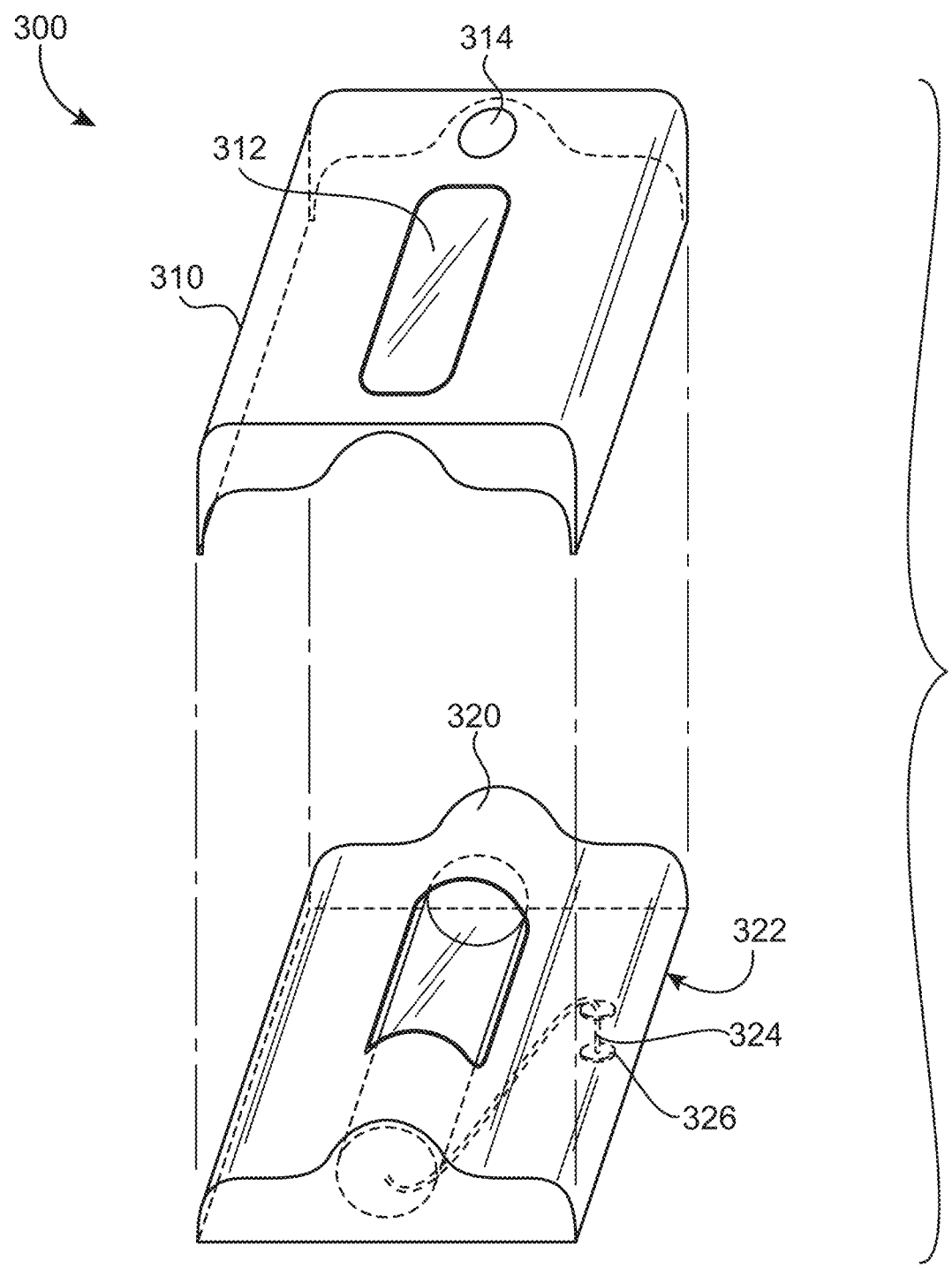
FIG. 10 is a perspective view of the bolus injector of FIG. 9.
Figure 11:
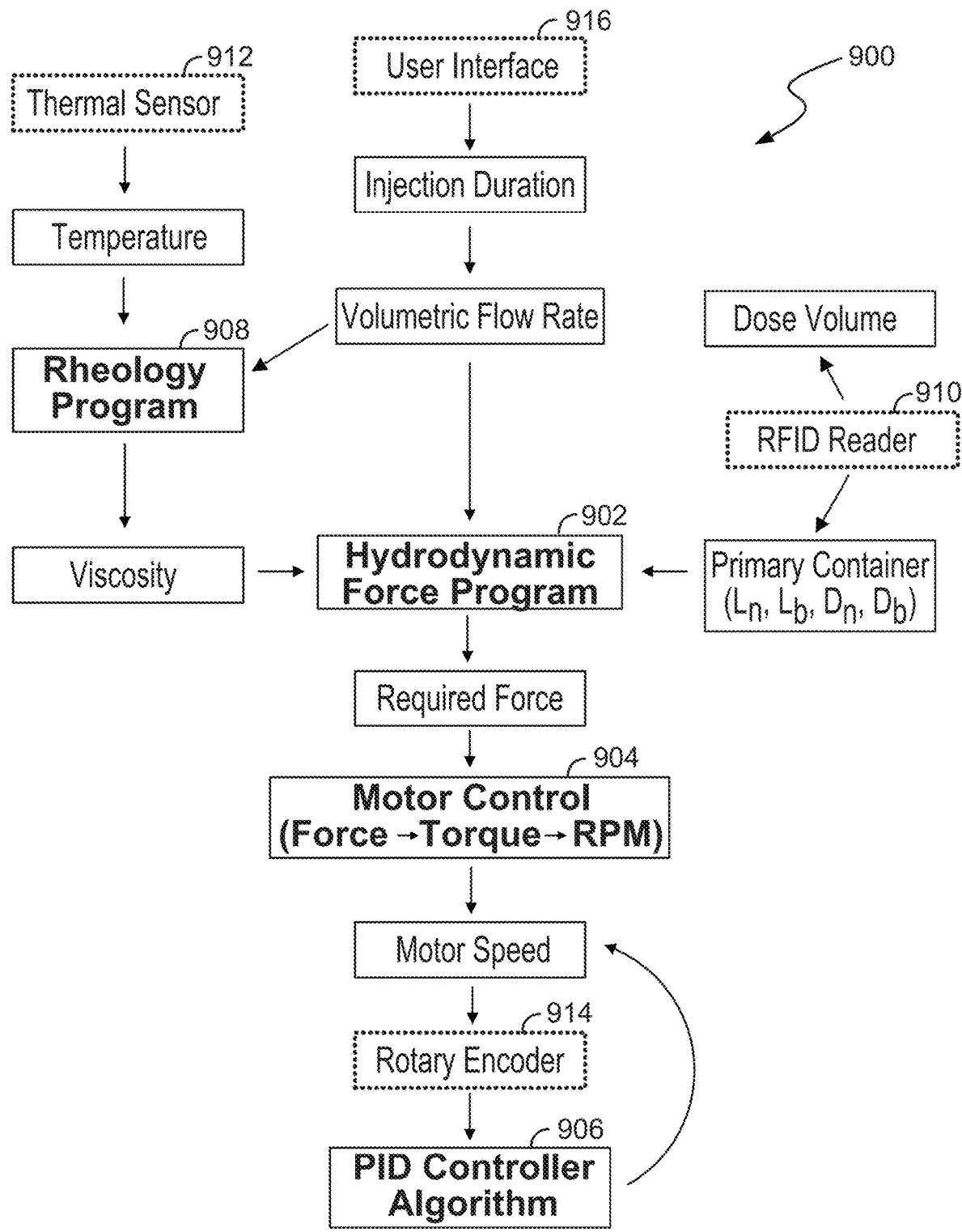
FIG. 11 is a block diagram illustrating a control system environment in which aspects of the injector technology may operate in various embodiments.

For example, in a further embodiment, the injection assembly components described above and illustrated in FIGS. 1A-5 can be assembled in a manner such that all the methods and features described above are achieved in a bolus injection device. FIG. 9 is a front view of a bolus injection device 300 for automated delivery of a liquid medicament to a subject 301 in accordance with an embodiment of the present technology. FIG. 10 is a perspective view of the bolus injection device 300 of FIG. 9. The bolus injection device 300 includes features generally similar to the features of the injection device 10 described above with respect to FIGS. 1A-5. In particular, the bolus injection device 300 includes a bolus injector 310 and a disposable dose module 320 receivable in the bolus injector 310 for delivery of the liquid medicament (e.g., visible through a window 312) to a subject 301. With reference to FIGS. 9 and 10 together, and in some embodiments, the bolus injector 310 is wearable by the subject 301, for example, by attaching the device 300 to the clothing of the subject 301, or in another arrangement, by attaching the device 300 to the skin 302 of the subject 301. In a particular example, the lower surface of the disposable dose module 320 (e.g., the cassette) can be configured to stick or adhere to the skin 302 of the subject 301, for example, via an adhesive surface 322 (FIG. 10) or the like. When the disposable dose module 320 is properly inserted into the bolus injector 310, the adhesive surface 322 of the dose module 320 may serve as a base for the injection device 300.

In some embodiments, the bolus injection device 300 is capable of delivering large volumes of high viscosity biological drugs. For example, the total delivered volume of medicament can be between about 1 mL and about 20 mL. In certain arrangements, the drive mechanism (not shown) for delivering the liquid medicament in a controlled manner is similar to the drive mechanism 110 described above and illustrated in FIGS. 1B, 2 and 5. In other embodiments, the rate of injection from a bolus injection device 300 described herein can be slower than conventional bolus injectors. For example, a maximum rate of delivery can be approximately 100 mL/hr. In certain arrangements, the rate of delivery is controllable by the user. In further embodiments, the rate of delivery can be recorded by the device 300 from the time the delivery of the liquid medicament begins to the completion of delivery. In yet a further embodiment, the bolus injection device 300 may be capable of stopping and restarting delivery. For example, the bolus injection device 300 may stop delivery based on improper flow rate, which can be indicative of a change in the viscosity of the liquid medicament. In additional arrangements, the subject 301 may stop delivery based on discomfort.

In some embodiments, the bolus injection device 300 is a programmable electronic device. For example, the electronic drive mechanism can be preprogrammed to deliver the liquid medicament at a specific flow rate. In certain embodiments, the bolus injector 310 (FIGS. 9 and 10) can become activated when a disposable dose module 320 (FIG. 10) is properly inserted into the base of the injector 310. In another embodiment, the bolus injector 310 can become activated when an activation button 314 on the injector is engaged by a user. In a further embodiment, the bolus injection device 300 alerts the user when the dose module 320 reaches an appropriate injection temperature by wirelessly sending a notification to a software application running on a user's device or computer. In yet further arrangements, the bolus injection device 300 can alert the user at the end of delivery, thereby indicating it is safe to remove the device. In another embodiment, the bolus injection device 300 can automatically upload the data related to the injection wirelessly to a software application.

In some embodiments, the drive path of the drive mechanism of the bolus injector 310 and the syringe (not shown) in the dose module 320 are aligned, and the direction of movement may be parallel to a base of the device 300. In some embodiments, the dose module 320 includes a hypodermic needle 324 and a needle release mechanism (not shown) for inserting the needle 324 through a needle aperture 326 disposed in the lower and/or adhesive surface 322 of the dose module 320 and into the skin 302 of the subject 301. In another embodiment, the direction of movement of the hypodermic needle 324 may be perpendicular to the base of the device 300. For example, the needle 324 may be inserted into the recipient's skin 302 at about a 90 degree angle. In other examples, the needle 324 may be inserted into the recipient's skin 302 at an angle less than about 90°. In some arrangements. the needle release may be synchronized to the injector's drive mechanism.

FIG. 1I is a block diagram illustrating the control system environment 900 in which aspects of the injector technology may operate in various embodiments. The environment 900 includes the sensors and controlled components discussed above with respect to FIGS. 1A-5. For example, the environment can include a processor and associated memory retaining instructions for one or more processes. Operative programs can include, for example, a hydrodynamic force program 902, a motor control program 904, proportional-integral-derivative (PID) controller instructions 906, and a rheology program 908. As discussed above, these processes can be based on injection data and other feedback data, such as data collected from an RFID reader 910, a thermal sensor 912, a rotary encoder 914 and a user interface 916. Instructions for operatively injecting a dosage into a patient can include instructions for determining the appropriate force provided by the motor to achieve a user-controlled injection time.

Table 1 describes a plurality of variables that can affect drug delivery force ($F_{total}$).

TABLE 1

Variables affecting Drug Delivery Force ($F_{total}$)

| Variable | Synonym | Unit | Physical Location of Data |
|---|---|---|---|
| Needle length (Ln) | | mm | Dose Module ID Tag |
| Needle radius (rn) | | mm | Dose Module ID Tag |
| Barrel radius (rb) | | mm | Dose Module ID Tag |
| Volume (V) | | mL | Dose Module ID Tag |
| Temperature (T) | | C. | Thermometer |
| Concentration (C) | | mg/mL | Dose Module ID Tag |
| Injection velocity (ϑ) | Plunger speed | mm/s | Injector (function) |
| Volumetric flow rate (Q) | | mL/s | Injector (function) |
| Shear rate (γ) | | l/s | Injector (function) |
| Power-law index (n) | Flow Index | Dimensionless | Injector (function) |

TABLE 1-continued

Variables affecting Drug Delivery Force ($F_{total}$)

| Variable | Synonym | Unit | Physical Location of Data |
|---|---|---|---|
| Flow consistency index (K) | Consistency | cP^n (mPa · s^n) | Injector (function) |
| Viscosity (μ) | Resistance to flow | cP (mPa · s) | Injector (function) |
| Spring Force (Fspring) | Needle Spring | N (kg · m/s^2) | Dose Module ID Tag |
| Tissue Force (Ftissue) | | N (kg · m/s^2) | Injector (constant) |
| Frictional Force (Ffriction) | | N (kg · m/s^2) | Injector (function) |
| Hydrodynamic Force (Fhydrodynamic) | Glide force | N (kg · m/s^2) | Injector (function) |

EXAMPLES

Example 1

The viscosity of a drug dose is primarily dependent on the drug concentration and the solution temperature. Therefore, in one example, it is possible to detect changes to the drug concentration based on drug delivery force, given a constant primary containment system and drug solution temperature. Specifically, drug delivery force measurement may be used to detect counterfeit drug doses (e.g. low or no drug concentration). For example, an experiment was performed to determine how the viscosity of a drug dose effects the drug delivery force of the injection. The experiment used a 27G×0.5" needle, a BD Tuberculin Syringe, 1 mL, Lure Slip Tip with a 57 mm syringe travel, an injection speed of 5 seconds and the GammaGard (1 g/10 ml) biologic. The experiment varied the concentration of the biologic to distilled water at 100 mg/mL (100%), 50 mg/mL (50%), and 0 mg/mL (0%) and was run at room temperature (average 26° C.) and refrigerator temperature (average 5° C.). Five samples for 100 mg/mL, 50 mg/mL, and 0 mg/mL concentrations at both refrigerator and room temperatures were tested, equaling a total of 30 test runs. After parsing the data, and averaging over the 5 trials, the average and standard deviation for each concentration for both room temperature and refrigerator temperature were obtained.

Figure 12:
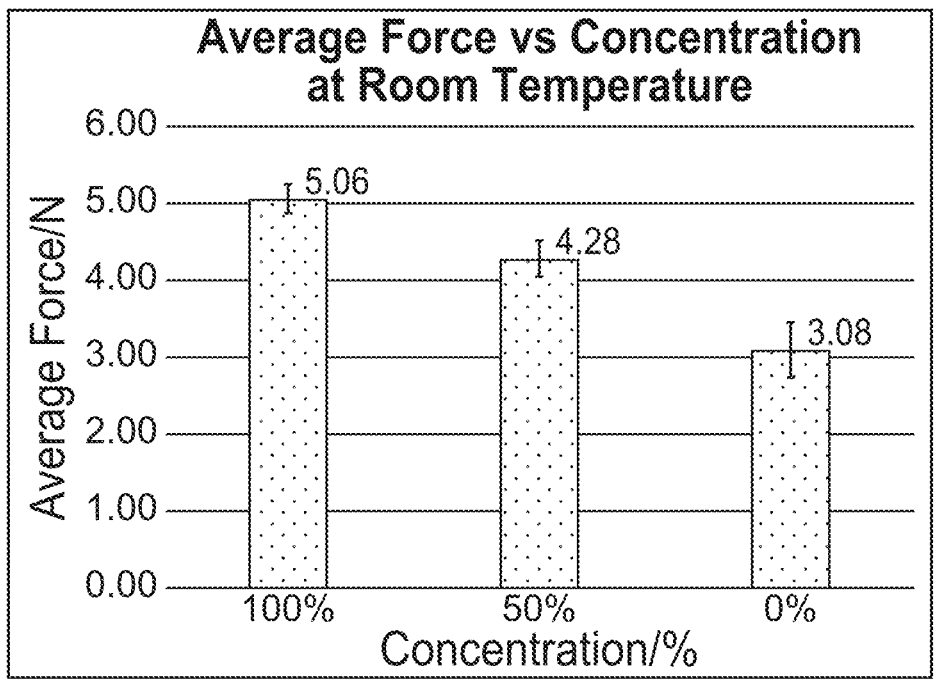
FIG. 12 is a bar graph indicating average drug delivery force relative to concentration measured at room temperature.
Figure 13:
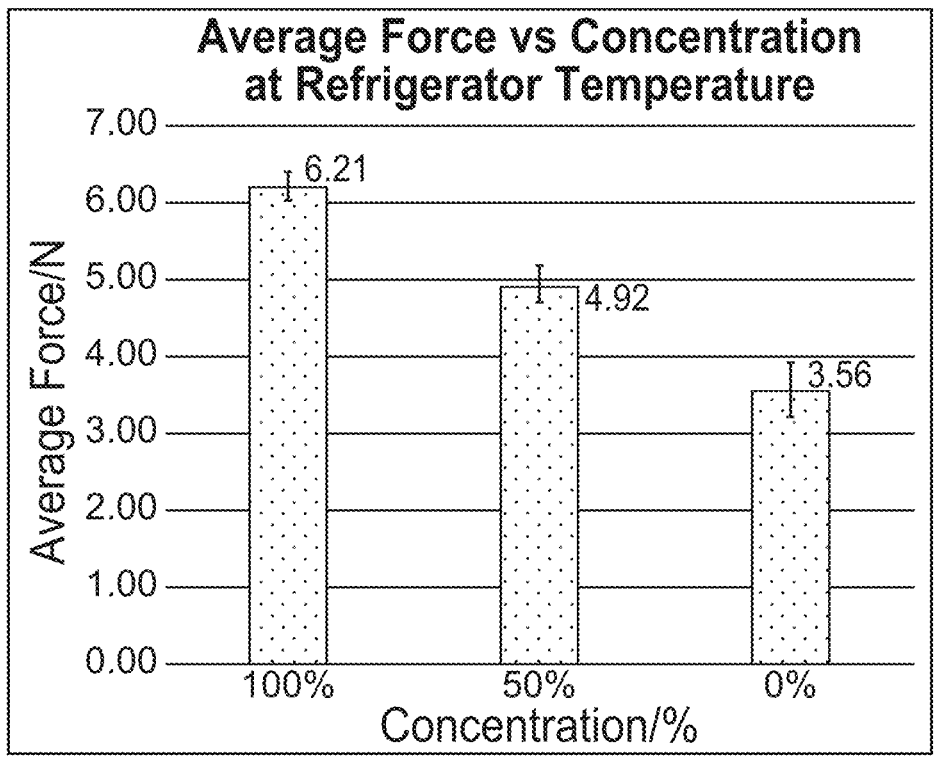
FIG. 13 is a bar graph indicating average drug delivery force relative to concentration measured at refrigerated temperature.

The bars in FIGS. 12 and 13 indicate the average drug delivery force relative to concentration, and the error bars indicate one standard deviation in either direction from the average. The different concentrations vary substantially with the average drug delivery force. Thus, drug viscosity determined by measuring drug delivery force of the drug dose actually administered compared to a standard benchmark performance of the drug dose can be used to detect whether the quality of a drug dose has been compromised.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term. respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for automated delivery of a liquid medicament to a subject from an injector assembly, the method comprising:
    positioning a cartridge carrying the liquid medicament in an internal cavity of an injector;
    receiving input to define one or more injection parameters;
    calculating an injection force; and
    initiating an injection of the liquid medicament using the injection force,
    wherein calculating the injection force comprises calculating a viscosity of the liquid medicament using at least a rheology program stored in a memory of the injector assembly, and wherein the rheology program is specific to the liquid medicament.

2. The method of claim 1, wherein receiving input comprises obtaining an injection speed for delivery of the liquid medicament from the cartridge to the subject.

3. The method of claim 1, wherein receiving input comprises detecting a temperature of the liquid medicament.

4. The method of claim 1, wherein receiving input comprises detecting identification information on a RFID tag on the cartridge.

5. The method of claim 1, wherein initiating the injection of the liquid medication using the injection force includes delivering the liquid medicament within a pre-selected delivery time.

6. The method of claim 1, further comprising sending a notification to the subject to remind the subject to inject the liquid medicament at a predetermined time.

7. The method of claim 1, further comprising detecting a difference between a calculated injection duration and an actual injection duration.

8. The method of claim 7, further comprising analyzing injection data following the injection to determine an error source for the difference between the calculated injection duration and the actual injection duration.

9. The method of claim 1, wherein the injector is a bolus injector, and wherein the bolus injector is wearable by the subject.

10. An injector assembly for automatically delivering a dose of a liquid medicament in a controlled manner, comprising:
- a dose module comprising a cartridge housing a hypodermic syringe, wherein the hypodermic syringe contains the dose of the liquid medicament, and wherein the hypodermic syringe is coupled to a hypodermic needle;
- an injector having an internal cavity for receiving the cartridge, the injector comprising:
  - a motor configured to move the hypodermic needle from a retracted position to an extended position;
  - a power source;
  - a controller in communication with the power source and a plurality of sensors, the controller having instruction for causing the injector to:
    - receive input from the plurality of sensors to define one or more injection parameters, and
    - calculate an injection force for delivering the dose of the liquid medicament in a controlled manner, wherein calculating the injection force comprises calculating a viscosity of the liquid medicament using at least a rheology program stored in a memory of the injector assembly, and wherein the rheology program is specific to the liquid medicament.

11. The injector assembly of claim 10, wherein the instructions for causing the injector to receive input comprises instructions for obtaining an injection speed for delivery of the dose of the liquid medicament from the cartridge.

12. The injector assembly of claim 10, wherein the instructions for causing the injector to receive input comprises instructions for detecting a temperature of the dose of the liquid medicament.

13. The injector assembly of claim 10, wherein the injector further comprises a radio transceiver for transmitting data related to a delivery of a dose of the liquid medicament.

14. The injector assembly of claim 10, wherein the injector further comprises a drive mechanism operably coupled to the controller, and wherein the controller controls the drive mechanism such that a speed of the motor is controlled based on the calculated injection force.

15. The injector assembly of claim 10, wherein the injector is a bolus injector.

* * * * *